United States Patent [19]

Sharpe

[11] 4,364,274

[45] Dec. 21, 1982

[54] ULTRASONIC INSPECTION WITH BACK ECHO MONITORING

[75] Inventor: Donald E. Sharpe, Woodbury, Conn.

[73] Assignee: Automation Industries, Inc., Greenwich, Conn.

[21] Appl. No.: 198,764

[22] Filed: Oct. 20, 1980

[51] Int. Cl.³ .......................................... G01N 29/04
[52] U.S. Cl. ..................................................... 73/615
[58] Field of Search .................. 73/615, 614, 616, 612, 73/631, 629

[56] References Cited

U.S. PATENT DOCUMENTS 3,738,159 6/1973 Donnadieu ............................ 73/615
4,098,130 7/1978 Coffey et al. .......................... 73/614

Primary Examiner—Stephen A. Kreitman
Attorney, Agent, or Firm—Francis N. Carten

[57] ABSTRACT

Method and apparatus for ultrasonic non-destructive testing by the pulse echo method. The pulses received from flaws in a test object are supplied to a main branch circuit for amplification to produce a suitable flaw display and to a back echo branch circuit having a lower amplification such that the back echo signal does not saturate the amplifier. During a "flaw gate" period, the output from the main branch circuit is supplied through a high speed electronic switch to a display. At the conclusion of the flaw gate period, the switch is actuated to supply the back echo branch circuit output to the display. In this manner, the back echo signal may be monitored for additional flaw information.

6 Claims, 4 Drawing Figures

ULTRASONIC INSPECTION WITH BACK ECHO MONITORING

TECHNICAL FIELD

The use of ultrasonics is well-known as a method for the non-destructive testing of materials. One of the more common procedures employs short bursts, or pulses, of ultrasonic energy from a transducer which is periodically electrically energized at a suitable frequency. These pulses penetrate the surface of the material, travel through it, and are reflected by discontinuities such as cracks and other flaws. The resultant "echoes" are detected by the same or a different transducer and are suitably displayed, as on an oscilloscope. In addition, the ultrasonic pulse is substantially fully reflected by the back surface of the test material and this "back echo" is also detected by the receiving transducer.

A conventional way of displaying the results of an ultrasonic test is to utilize an oscilloscope with the received pulses displayed along a time axis. Such a display would normally include a pulse reflected from the entrance surface, smaller pulses received from any flaws within the material, and the back surface echo.

Although primary interest lies in the detection of flaws within the material and determinations of their locations and sizes, the back surface echo is also of importance. The reason for this is that some defects may be oriented in such a manner that pulses echoing from them are deflected away from the receiving transducer. However, the presence of such a flaw could then be determined by a diminution of the back echo signal. A problem arises, however, from the fact that the echo flaw signals are much smaller than the back echo signal. If the receiver gain is increased sufficiently to display flaw signals, the back echo signal is in saturation so that changes in its amplitude are not displayed.

BACKGROUND ART

The conventional method of overcoming the foregoing problem, is to employ a time gate coinciding with the time required for signals to return from flaws closely adjacent the back surface. A suitably large gain during this period permits their display. A second gate is then employed whose start is slaved to the end of the flaw monitoring gate and is of sufficient length to contain the back echo. During the time period occupied by this back echo gate, a gain reduction signal is fed to the receiver in order to bring the back echo into the receiver's linear range. The problem which arises, however, is that the rapid change in gain which is required to bring the back echo into linear range causes detrimental side effects such as spurious signals at the gate edges.

It is a primary object of the present invention to provide ultrasonic pulse echo method and apparatus for accurately observing both flaw signals and changes in the back echo signal. Other objects are to provide such method and apparatus which avoid saturation of the receiver, which avoid transients and spurious side effects, and which do not require complex electronics or apparatus. Other objects, features and advantages will become apparent from the following description and appended claims.

DISCLOSURE OF INVENTION

An improvement in the method of examining a test object for internal flaws in which ultrasonic pulses are transmitted into an entry surface of the object and echoes of the pulses from the flaws and a back surface of the object are detected, converted into corresponding electrical signals, and displayed. In accordance with the improvement, a main branch circuit is established which includes a first level of amplification for echo signals which originate from flaws intermediate the entry and back surfaces. A back echo branch circuit is established which includes a second, lower, non-saturating level of amplification for echo signals originating from the back surface. The electrical signals are then selectively switched alternately through the main branch circuit and the echo branch circuit in order to achieve useful amplification of the flaw signals while avoiding amplifier saturation by the back echo signals.

BEST MODE FOR CARRYING OUT THE INVENTION

Figure 1:
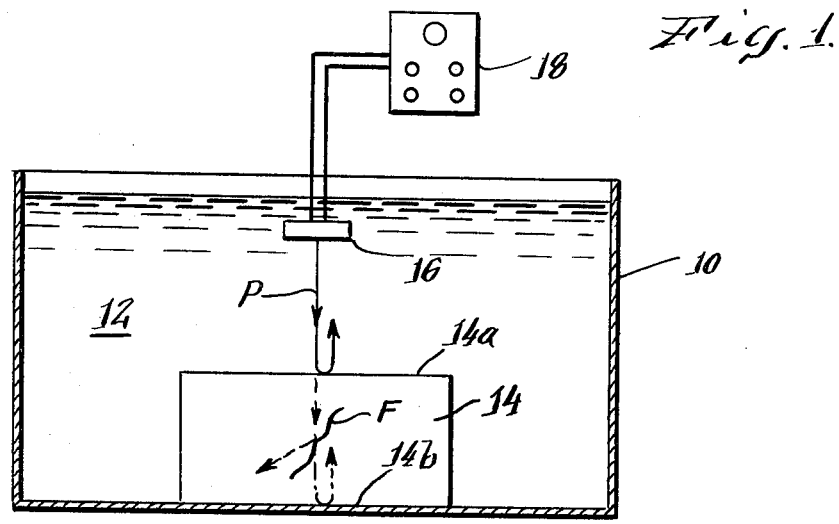
FIG. 1 is a diagrammatic illustration of an ultrasonic pulse echo test set-up.

With particular reference to FIG. 1, there is illustrated a tank 10 filled with a suitable ultrasonic coupling fluid 12 such as water. Immersed within the fluid is a test object 14 to be examined. An ultrasonic transducer 16 is positioned in the fluid 12 above the test object 14 and is connected to suitable energizing and display apparatus 18 which may include, for example, an oscilloscope. The transducer 16 is periodically energized with electrical pulses which produce corresponding ultrasonic pulses. These follow the paths P indicated by the solid and dashed lines with arrowheads. As illustrated, the ultrasonic pulses are reflected first by an entrance surface 14a of object 14, and also by its back surface 14b. FIG. 1 also illustrates the existence of a flaw F in the form of a crack oriented in such a manner as to divert the pulse echoes away from the transducer 16. The presence of such a flaw, however, could be inferred from the diminished amplitude of the echo from back surface 14b.

Figure 2:
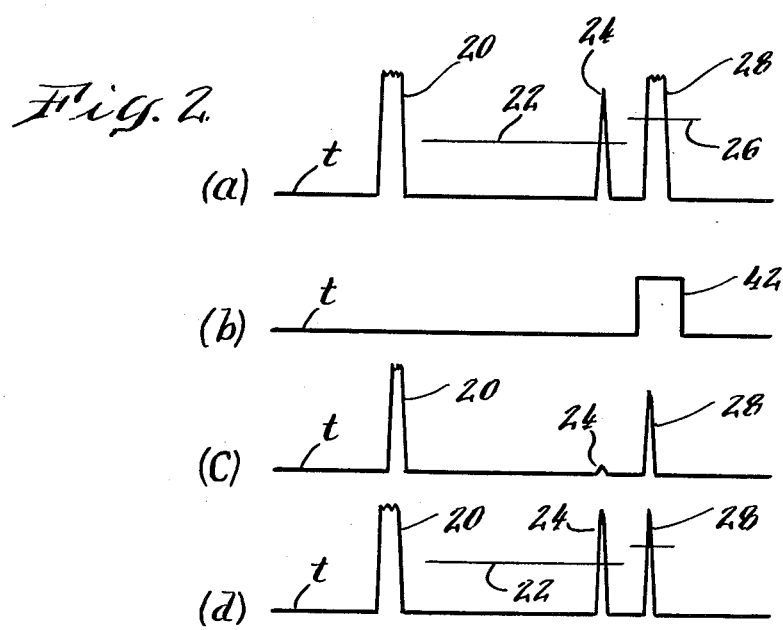
FIG. 2 is a set of four timing diagrams illustrating the operation of the circuit of this invention.

FIGS. 2(a)–(d) represent, along a time base, the various signals with which this invention is concerned. In FIG. 2(a), which represents the output of amplifier 30 and the gates, there is illustrated the entry surface signal 20. Shortly after the occurrence of the entry surface signal, there is established a defect gate for a period represented by line 22. During this period, defect signals such as signal 24 are detected and suitably amplified. Upon the conclusion of the defect gate period, a back echo gate 26 is established during which the back surface echo 28 is received.

Figure 3:
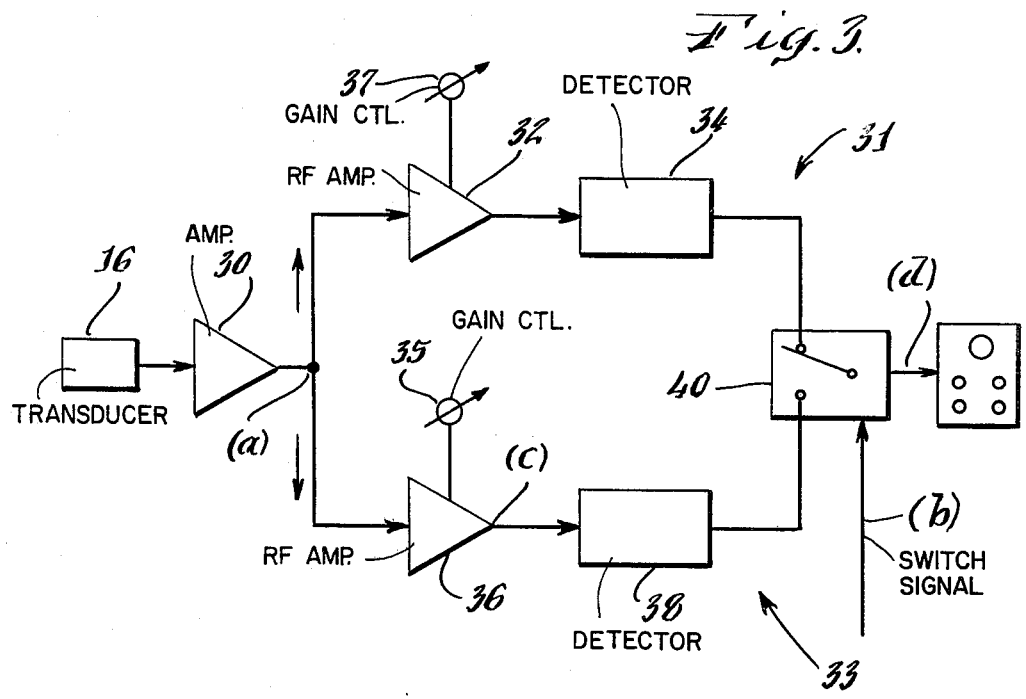
FIG. 3 is a block diagram of a circuit in accordance with the present invention.

Turning now to FIG. 3, there is disclosed a circuit in accordance with this invention which includes an amplifier 30 having one or more stages of RF amplification which receives the signal from transducer 16 and which has, as its output, signals of the form illustrated in FIG. 2(a). This output may be supplied simultaneously to both of two branch circuits, a main branch 31 comprising an RF amplifier 32 and detector 34, or a back echo branch circuit 33 comprising RF amplifier 36 and detector 38. The gain control 35 of the back echo amplifier 36 is set substantially lower than the gain control 37 of the RF amplifier 32 in order to maintain the back surface echo signal within the linear range of the amplifier. A high speed electronic switch 40 is operable by a back echo switching signal 42, as shown in FIG. 2(b), which is coincident with the back echo gate 26 of FIG. 2(a). During the defect gate period, the switch 40 is in the position illustrated in FIG. 3 to pass the amplified defect gate signal through the amplifier 32 and detector 34 to the CRT display. However, the back echo switching signal 42 serves to activate the electronic switch 40 to thereupon connect the back echo branch of the circuit to the CRT display. The output of the back echo branch is illustrated in FIG. 2(c). This branch, as previously explained, has a substantially reduced gain so that the back surface echo signal 28 is no longer in saturation but, rather, falls within the linear range of the amplifier thereby permitting variations in its amplitude to be observed.

It will be observed that the high speed electronic switch 40 is caused to create a multiplexing action. In other words, during the defect gate period, the defect signal 24, amplified as shown in FIG. 2(a), is passed to the CRT display. At the end of the defect gate, however, the switch is activated to permit the back echo signal 28, reduced in amplitude as illustrated in FIG. 2(c), to pass to the CRT display. The CRT display thus becomes a composite as illustrated in FIG. 2(d) wherein both the defect signal and the back surface signal fall within the linear region of the amplifier, thereby permitting observations of changes in amplitude.

Figure 4:
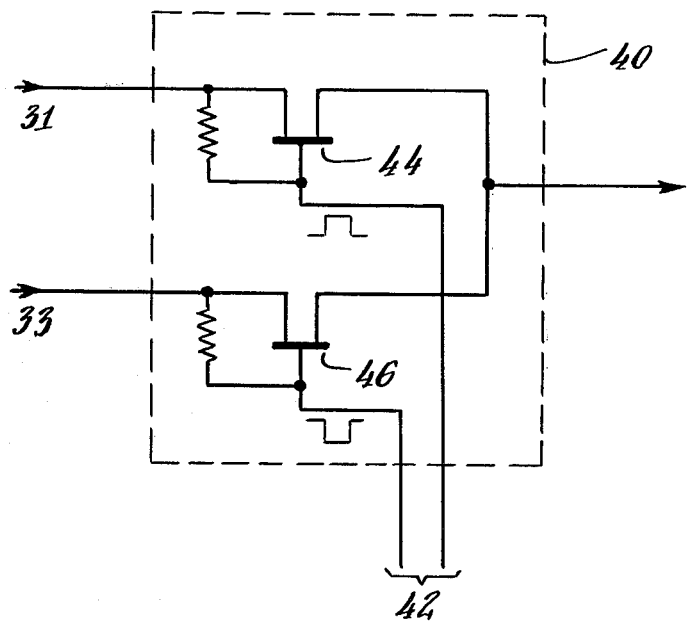
FIG. 4 is a schematic illustration of an electronic switch usable in the present invention.

Various types of electronic switches may be employed in this invention. One form of such a switch 40 is illustrated in FIG. 4 and is shown to include a pair of FET transistors 44, 46 which are connected, respectively, to the main branch and the back echo branch for activation by switching signal 42. It will be understood that a number of other variations and modifications may be made in this invention without departing from its spirit and scope. Accordingly, the foregoing description is to be construed as illustrative, rather than limiting. This invention is limited only by the scope of the following claims.

What is claimed is:

1. In the method of examining a test object for internal flaws wherein ultrasonic pulses are transmitted into an entry surface of said object and echoes of said pulses from flaws and from a back surface of said object are detected, converted into corresponding electrical signals, and displayed, the improvement which comprises:

establishing a main branch circuit including a first level of amplification for echo signals originating from flaws intermediate said entry and back surfaces;

establishing a back echo branch circuit including a second, lower, non-saturating level of amplification for echo signals originating from said back surface; and selectively switching said electrical signals alternately through said main branch circuit and said back echo branch circuit to achieve useful amplification of flaw signals while avoiding amplifier saturation by back echo signals.

2. The improvement of claim 1 wherein the electrical signals so switched form a composite display including flaw signals amplified at said first level of amplification and a back echo signal amplified at said second level of amplification.

3. In apparatus for examining a workpiece for internal flaws including an ultrasonic transducer for sending pulses of ultrasonic energy into an entry surface of said workpiece, the same or a different transducer for receiving ultrasonic pulses from internal flaws and a back surface of said workpiece and converting them into corresponding electrical signals, means for periodically electrically energizing said sending transducer, means for amplifying electrical signals from said receiving transducer, and means for utilizing said amplified signals, the improvement wherein said amplifying means comprises:

a main circuit having a first level of amplification for echo signals originating from flaws intermediate said entry and back surfaces;

a back echo circuit having a second, lower, nonsaturating level of amplification for echo signals originating from said back surface; and means for selectively switching said electrical signals alternately through said main circuit and said back echo circuit to achieve useful amplification of flaw signals while avoiding amplifier saturation by back echo signals.

4. The improvement of claim 3 wherein said switching means comprises a high speed electronic switch.

5. The improvement of claim 4 wherein said switch comprises:

a switching transistor in series with each of said main and back echo circuits; and means for alternately triggering said transistors between their conductive and non-conductive states.

6. The improvement of claim 5 wherein said transistors are field effect transistors.

* * * * *